(12) United States Patent
Mehner et al.

(10) Patent No.: US 12,185,992 B2
(45) Date of Patent: Jan. 7, 2025

(54) INTRAMEDULLARY NAIL SYSTEM

(71) Applicant: Mayo Foundation for Medical Education and Research, Rochester, MN (US)

(72) Inventors: Christine Mehner, Neptune Beach, FL (US); Marion T. Turnbull, Neptune Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 571 days.

(21) Appl. No.: 17/297,947

(22) PCT Filed: Dec. 6, 2019

(86) PCT No.: PCT/US2019/064984
§ 371 (c)(1),
(2) Date: May 27, 2021

(87) PCT Pub. No.: WO2020/118204
PCT Pub. Date: Jun. 11, 2020

(65) Prior Publication Data
US 2022/0079634 A1     Mar. 17, 2022

Related U.S. Application Data

(60) Provisional application No. 62/776,298, filed on Dec. 6, 2018.

(51) Int. Cl.
*A61B 17/72* (2006.01)
*A61B 17/88* (2006.01)
(Continued)

(52) U.S. Cl.
CPC ...... *A61B 17/7233* (2013.01); *A61B 17/8872* (2013.01); *A61B 17/90* (2021.08); *A61B 2017/681* (2013.01)

(58) Field of Classification Search
CPC ............ A61B 17/7216; A61B 17/7225; A61B 17/7233; A61B 17/88; A61B 17/90; A61B 17/8872; A61B 2017/681
See application file for complete search history.

(56) References Cited

U.S. PATENT DOCUMENTS

| | | |
|---|---|---|
| 3,530,854 A | 9/1970 | Kearney |
| 4,946,459 A | 8/1990 | Bradshaw et al. |

(Continued)

FOREIGN PATENT DOCUMENTS

WO    WO 2003043508    5/2003

OTHER PUBLICATIONS

Choi et al., "A novel smart navigation system for intramedullary nailing in orthopedic surgery," PLoS One, Apr. 17, 2017, 12(4):e0174407, 20 pages.

(Continued)

*Primary Examiner* — Julianna N Harvey
*Assistant Examiner* — Angel Roberto Mora-Velazquez
(74) *Attorney, Agent, or Firm* — Fish & Richardson P.C.

(57) ABSTRACT

Intramedullary nails can be used for the treatment of a bone fracture. In some embodiments, such intramedullary nails can include an elongate shaft having a longitudinal axis, a distal nail component, and a proximal nail component. In some embodiments, the intramedullary nails include a first rotatable shaft and a second rotatable shaft. In some embodiments, the intramedullary nails include a handle coupled to the first and second rotatable shafts.

22 Claims, 5 Drawing Sheets

(51) Int. Cl.
*A61B 17/90* (2006.01)
*A61B 17/68* (2006.01)

(56) References Cited

U.S. PATENT DOCUMENTS

| | | | |
|---|---|---|---|
| 5,100,404 A | 3/1992 | Hayes | |
| 8,388,627 B2 | 3/2013 | Panchbhavi | |
| 2005/0096655 A1* | 5/2005 | Trinchese | A61B 17/1707 606/62 |
| 2008/0255573 A1* | 10/2008 | Willett | A61B 90/11 606/96 |
| 2013/0325008 A1* | 12/2013 | Kuxhaus | A61B 17/744 606/63 |
| 2016/0183994 A1* | 6/2016 | Quach | A61B 50/30 606/90 |
| 2018/0344377 A1* | 12/2018 | McManus | A61B 17/72 |
| 2023/0301646 A1* | 9/2023 | Duggal | A61B 17/683 |

OTHER PUBLICATIONS

Goodall, "An image intensifier laser guidance system for the distal locking of an intramedullary nail," Injury, Jul. 1991, 22(4):339.

PCT International Preliminary Report on Patentability in International Appln. No. PCT/US2019/064984, dated Mar. 5, 2020, 7 pages.

PCT International Search Report and Written Opinion in International Appln. No. PCT/US2019/064984, dated Mar. 5, 2020, 9 pages.

Sanatmetal.hu [online], "Magic Tibia nail," upon information and belief, available no later than Dec. 6, 2018, retrieved on Oct. 15, 2021, retrieved from URL<https://sanatmetal.hu/en/product/magic-tibia-nail/>, 3 pages.

Zimmer, "Zimmer Natural Nail System: Tibial Nail Surgical Suprapatella Technique," dated Jun. 26, 2015, 26 pages.

* cited by examiner

INTRAMEDULLARY NAIL SYSTEM

CROSS-REFERENCE TO RELATED APPLICATIONS

This application is a National Stage application under 35 U.S.C. § 371 of International Application No. PCT/US2019/064984, having an International Filing Date of Dec. 6, 2019, which claims priority to U.S. Application Ser. No. 62/776,298, filed on Dec. 6, 2018. The disclosure of the prior applications are considered part of the disclosure of this application, and are incorporated in its entirety into this application.

BACKGROUND

1. Technical Field

This document relates to devices, systems, and methods for treating a bone fracture. For example, this document relates to devices, systems, and methods of intramedullary nailing for bone fractures.

2. Background Information

Each year about 1.5 million long bone fractures occur in the US alone. High velocity trauma can lead to fractures of the tibia or femur shaft, and falls can easily result in fractures of the humerus. If indicated patients receive an intramedullary nail which bridges the fracture and stabilizes the bone. Surgical outcomes are generally correlated with the experience of the surgeon, however, in the case of complex fractures, surgeries are lengthy, the correction can be unstable (the fracture can slip out of the perfect position) and there is a risk that the bone angle is incorrectly placed. In lower limb realignments, angle misalignment of over 10° can result in severe long term impairment and disability for the patient, and have a major impact on the alignment of all the adjacent joints. This disclosure addresses the need for patient-specific correct angle alignment during long bone fracture surgeries.

SUMMARY

The present disclosure describes intramedullary nail systems used for bone fractures, and more particularly to laser-guided, angle-correcting intramedullary nail systems.

The intramedullary nail system of the disclosure is a top and bottom two component nail which is inserted into the fractured bone (e.g., tibia, femur, and humerus) and fixed at the distal end with screws through the bone. The internal rotating mechanism is used to push the distal part of the nail—along with the distal limb (which moves freely due to the fracture)—and internally "open" the fracture site. A positioning laser mounted to the nail-insertion handle will then act as a guide for positioning the foot in line with the tibia plateau. Using a second internal rotating mechanism it will be possible to directly fine adjust the angle of the distal limb to the normal physiological angle. The nail is designed in such way that the distal part now moves independent from the proximal portion of the nail and the angle can be adjusted with precision using a special tool inserted into the nail. Once the perfect angle is determined steps are done in reverse, the nail and with it the fracture is "closed" by retracting the distal part of the nail, keeping the angle secure and locked. At this point the outer shell interlocks between the distal and the proximal part of the nail, making it stable and allowing for weight bearing.

In one aspect, this disclosure is directed to an intramedullary nail for treating a bone fracture. The intramedullary nail includes an elongate shaft defining a longitudinal axis and comprising a distal nail component and a proximal nail component, the proximal nail component defining a first coaxial channel that is coaxial with the elongate shaft, the distal nail component defining a second coaxial channel that is coaxial with the first coaxial channel; a first rotatable shaft disposed within the first coaxial channel, the first rotatable shaft rotatable relative to the longitudinal axis, the first rotatable shaft defining a third coaxial channel; a second rotatable shaft disposed within the second and third coaxial channels, the second rotatable shaft being rotatable relative to the longitudinal axis, the second rotatable shaft fixedly coupled to the distal nail component; and a handle extending from the proximal nail component, the handle coupled to the first and second rotatable shafts.

In some embodiments, the first coaxial channel has a first diameter that is greater than a second diameter of the second coaxial channel. In some embodiments, the first rotatable shaft is a threaded shaft. In some embodiments, the first coaxial channel comprises threads that facilitate engagement of the threaded shaft. In some embodiments, the elongate shaft is extendable. In some embodiments, the intramedullary nail further includes a lock for securing a position of the proximal nail component relative to the distal nail component. In some embodiments, the distal nail component is rotatable relative to the longitudinal axis.

In another aspect, this disclosure includes an orthopedic system for treating a bone fracture. The orthopedic system includes an intramedullary nail including an elongate shaft having a longitudinal axis, a distal nail component, and a proximal nail component, the proximal nail component defining a first coaxial channel that is coaxial with the elongate shaft, the distal nail component defining a second coaxial channel that is coaxial with the first coaxial channel; a first rotatable shaft disposed within the first coaxial channel, the first rotatable shaft being rotatable relative to the longitudinal axis, the first rotatable shaft defining a third coaxial channel; a second rotatable shaft disposed within the second and third coaxial channels, the second rotatable shaft being rotatable relative to the longitudinal axis, the second rotatable shaft coupled to the distal nail component; and a handle extending from the proximal nail component, the handle coupled to the first and second rotatable shafts; and a laser alignment device mounted onto the handle.

In some embodiments, the first coaxial channel has a first diameter that is greater than a second diameter of the second internal coaxial channel. In some embodiments, the first rotatable shaft is a threaded shaft and the second coaxial channel comprises threads that facilitate engagement of the threaded shaft. In some embodiments, the elongate shaft is an extendable shaft. In some embodiments, the orthopedic system further includes a lock for securing a position of the proximal nail component, the distal nail component, or both of the proximal and distal nail components. In some embodiments, the distal nail component is rotatable about the longitudinal axis. In some embodiments, the laser alignment device emits a laser beam. In some embodiments, the laser alignment device the laser beam aligns the intramedullary nail with a bone having the bone fracture, a foot of a subject having the bone fracture, or both the bone having the bone fracture and the foot of a subject having the bone fracture.

In another aspect, this disclosure is directed to a method of using an orthopedic system for treating a fractured bone of a subject. The method includes boring a bone channel in the fractured bone; inserting an elongate shaft of an intramedullary nail into the bone channel of a proximal portion and a distal portion of the fractured bone; pushing a distal nail component of the intramedullary nail distally by using a first rotatable shaft disposed within a first coaxial channel of a proximal nail component of the intramedullary nail; adjusting an angle of the distal nail component relative to a longitudinal axis of the elongate shaft using a laser alignment device and by rotating a second rotatable shaft disposed within: (i) a second coaxial channel of the distal nail component and (ii) a third coaxial channel defined by the first rotatable shaft; and retracting the distal nail component proximally to interlock with the proximal nail component and to secure the angle.

In some embodiments, the bone is a long bone. In some embodiments, the bone channel comprises a medullary canal of the fractured bone. In some embodiments, the method further includes reaming the medullary canal of the fractured bone. In some embodiments, pushing the distal nail component of the intramedullary nail distally comprises separating the proximal portion and the distal portion of the fractured bone. Such an intramedullary nail system may optionally include one or more of the following features.

Particular embodiments of the subject matter described in this document can be implemented to realize one or more of the following advantages. In some embodiments, the intramedullary nail systems provided herein can reduce the dependence on highly experienced surgeons, can reduce surgery times and costs, can prevent long term impairment for the patient, and can reduce associated health care costs.

Furthermore, the intramedullary nail systems provided herein can prevent malrotation and malunion of a bone in a patient during an intramedullary bone nailing. For example, the intramedullary nail systems of the disclosure allow a user (e.g., a medical provider) to directly fine adjust the angle of a fractured limb during surgery. The nail is designed in such way that the distal part now moves independent from the proximal portion of the nail and the angle can be adjusted with precision using a special tool inserted into the nail. Once the perfect angle (i.e., an angle that is equivalent to the natural, physiological angle) is determined, steps are done in reverse, the nail and with it the fracture is "closed" by retracting the distal part of the nail, keeping the angle secure and locked. This could have an immense positive impact on both short term fracture health as well as long term joint health by providing perfect angle alignment. Additionally, the intramedullary nail systems provided can be used for various fracture sites (e.g., tibia, femur, and humerus) and any other bone fracture that would require angle alignment.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The use of the term "about," as used herein, refers to an amount that is near the stated amount by about 10%, 5%, or 1%, including increments therein. For example, "about" can mean a range including the particular value and ranging from 10% below that particular value and spanning to 10% above that particular value.

The term "subject," as used herein refers to any mammal (e.g., a human or a veterinary subject, e.g., a dog, cat, horse, cow, goat, sheep, mouse, rat, or rabbit).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 is an exploded view of an example intramedullary nail.

Like reference symbols in the various drawings indicate like elements.

DETAILED DESCRIPTION

The present disclosure describes orthopedic systems, devices, and methods for the treatment of bone fractures. More particularly, this document provides laser-guided, angle-correcting intramedullary nail systems, devices, and methods. While intramedullary nailing of a long bone of a leg is used as the context to describe the devices, systems, and methods provided herein, it should be understood that the devices, systems, and methods may also be used in various other suitable contexts. For example, devices, systems, and methods provided herein may be used for the treatment of any long bone in a body of a subject.

Figure 1:
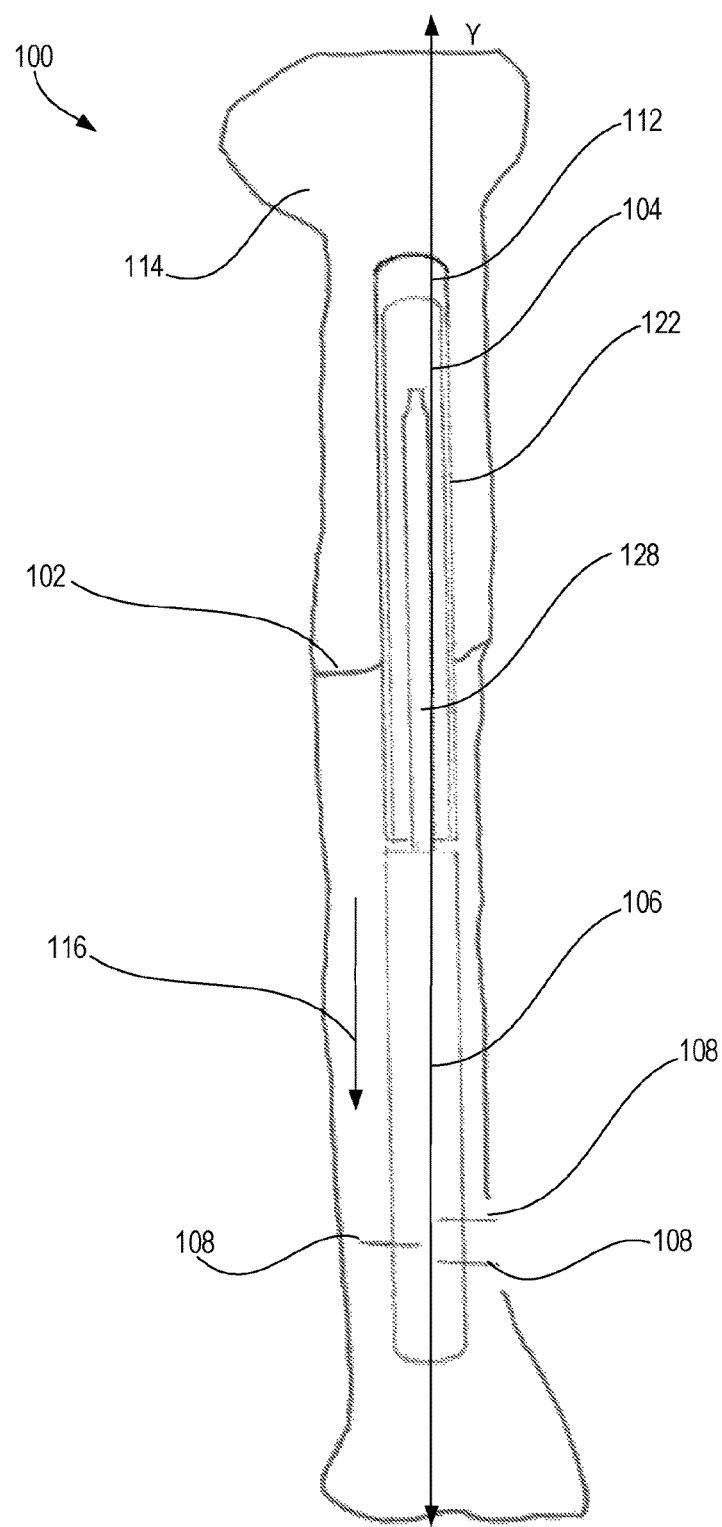
FIG. 1 is a partial cutaway view of an intramedullary nail in accordance with some embodiments provided herein.

Referring to FIG. 1, an example intramedullary nail 100 inserted within a bone 114 having a fracture 102 is shown. In some embodiments, the intramedullary nail 100 can have a length of about 50 centimeters (cm) or less (e.g., 45 cm or less, 40 cm or less, 35 cm or less, 30 cm or less, 25 cm or less, 20 cm or less). In some embodiments, the intramedullary nail 100 can have a diameter of about 20 millimeters (mm) or less (e.g., 15 mm or less, 10 mm or less, 9 mm or less, 8 mm or less, 7 mm or less, 6 mm or less, 5 mm or less, 4 mm or less). The intramedullary nail 100 includes an elongate shaft having a longitudinal axis Y. The intramedullary nail 100 includes a proximal nail component 122 and a distal nail component 106. In some embodiments, the proximal nail component 122 can have a length of about 30 centimeters (cm) or less (e.g., 25 cm or less, 20 cm or less, 15 cm or less, 10 cm or less, 5 cm or less). In some embodiments, the a distal nail component 106 can have a length of about 30 centimeters (cm) or less (e.g., 25 cm or less, 20 cm or less, 15 cm or less, 10 cm or less, 5 cm or less). In some embodiments, the distal nail component 106 is curved. In some embodiments, the distal nail component 106 is straight. In some embodiments, the proximal nail component 122 and the distal nail component 106 are shaped like a long bone. As used to herein, the term "long bone" is defined as any of the elongated bones supporting a vertebrate limb and including an essentially cylindrical shaft that contains bone marrow and ends in enlarged heads for articulation with other bones. In some embodiments, the long bone is a humerus, a fibula, a tibia, a radius, a clavicle, or any combination thereof. The proximal nail component 122 defines a first coaxial channel. The distal nail component 106 defines a second coaxial channel. The proximal nail component 122 includes an outside cover 112 that houses the first rotatable shaft 104. The proximal nail component 122 includes a first rotatable shaft 104 that is disposed within the first coaxial channel. The proximal nail component 122 includes an outside cover 112 that houses the first rotatable shaft 104. The first rotatable shaft 104 can be a threaded shaft that engages with a threaded inner wall of the first coaxial channel. That is, the first coaxial channel can include threads that facilitate engagement of the threaded shaft. The first rotatable shaft 104 defines a third coaxial channel. The first coaxial channel can have a first diameter that is greater than a second diameter of the second coaxial channel.

The intramedullary nail 100 further includes a second rotatable shaft 128. The second rotatable shaft 128 is disposed within the second and third coaxial channels and thus, can extend through the proximal nail component 122 and the distal nail component 106. The second rotatable shaft 128 is coupled to the distal nail component 106. The proximal nail component 122 and the distal nail component 106 can be connected via the second rotatable shaft 128. The elongate shaft of the intramedullary nail 100 can be an extendable shaft. For example, the distal nail component 106 can be pushed distally away from the proximal nail component 122, as shown by arrow 116, and extended. The distal nail component 106 further includes one or more holes at its distal end that receive screws 108. Screws 108 are secured onto the intramedullary nail to fixate and thereby treat the fractured bone.

Figure 2:
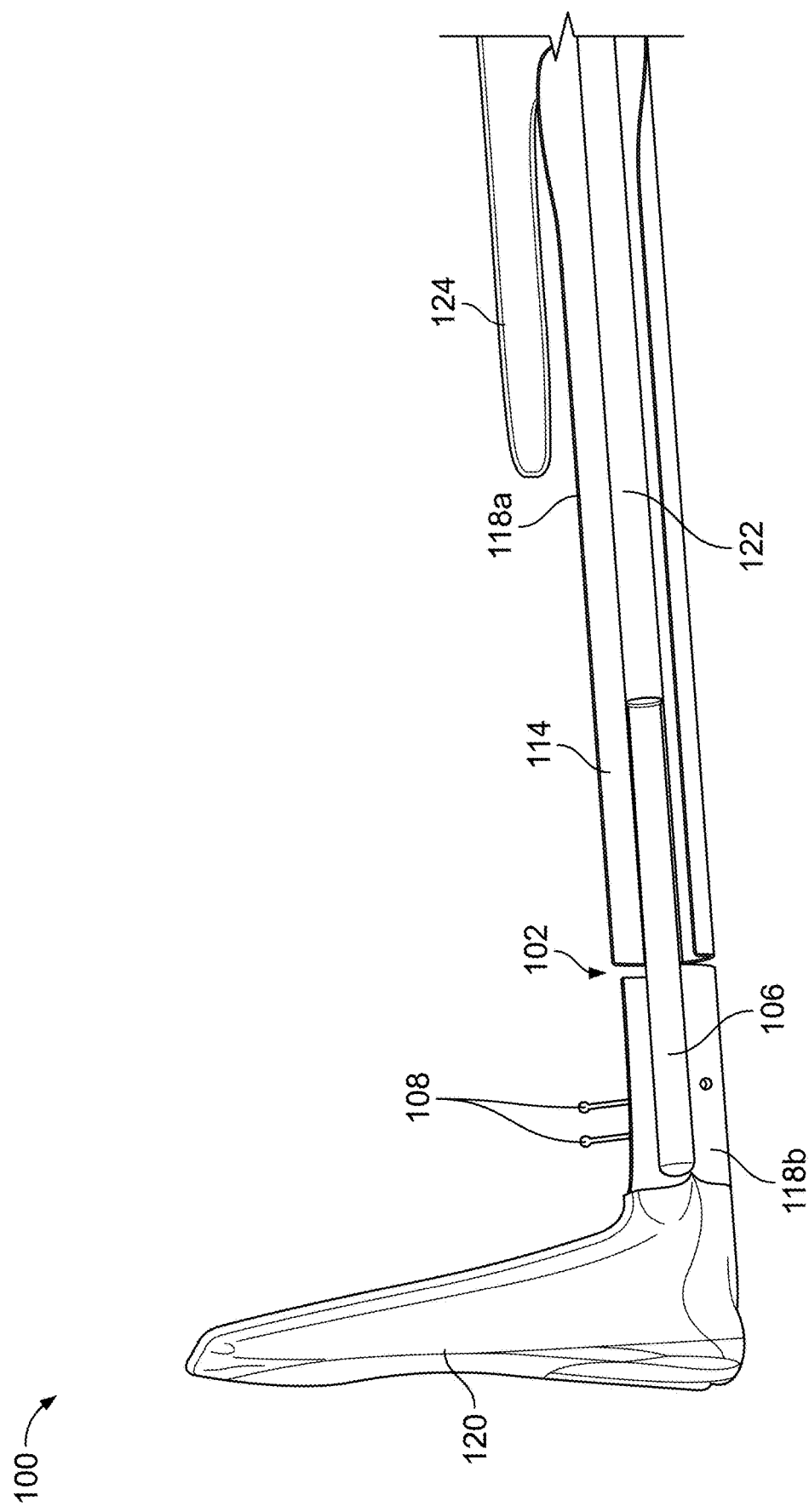
FIG. 2 is a side, partial cutaway view of an example orthopedic system inserted into a fractured bone of a subject.

Referring to FIG. 2, an example intramedullary nail 100 inserted within a bone 114 having a fracture 102 is shown. Fracture 102 can be any type of bone fracture such as, but not limited to, a stable fracture, an open, compound fracture, a transverse fracture, an oblique fracture, or a comminuted fracture. In this example, the bone 114 is a long bone of a leg that is connected to a foot 120 of a subject. Furthermore, in this example, fracture 102 separates a proximal portion 118a of the bone 114 and a distal portion 118b of the bone 114. The intramedullary nail 100 further includes a nail insertion handle 124 that can aid the user (e.g., a medical practitioner) to insert the intramedullary nail 100 into a bone channel within bone 114. In some embodiments, the user can use a mallet to insert the intramedullary nail 100 into a bone channel within bone 114. Screws 108 can be used to fix the distal nail component 106 to the distal portion 118b of bone 114.

Figure 3:
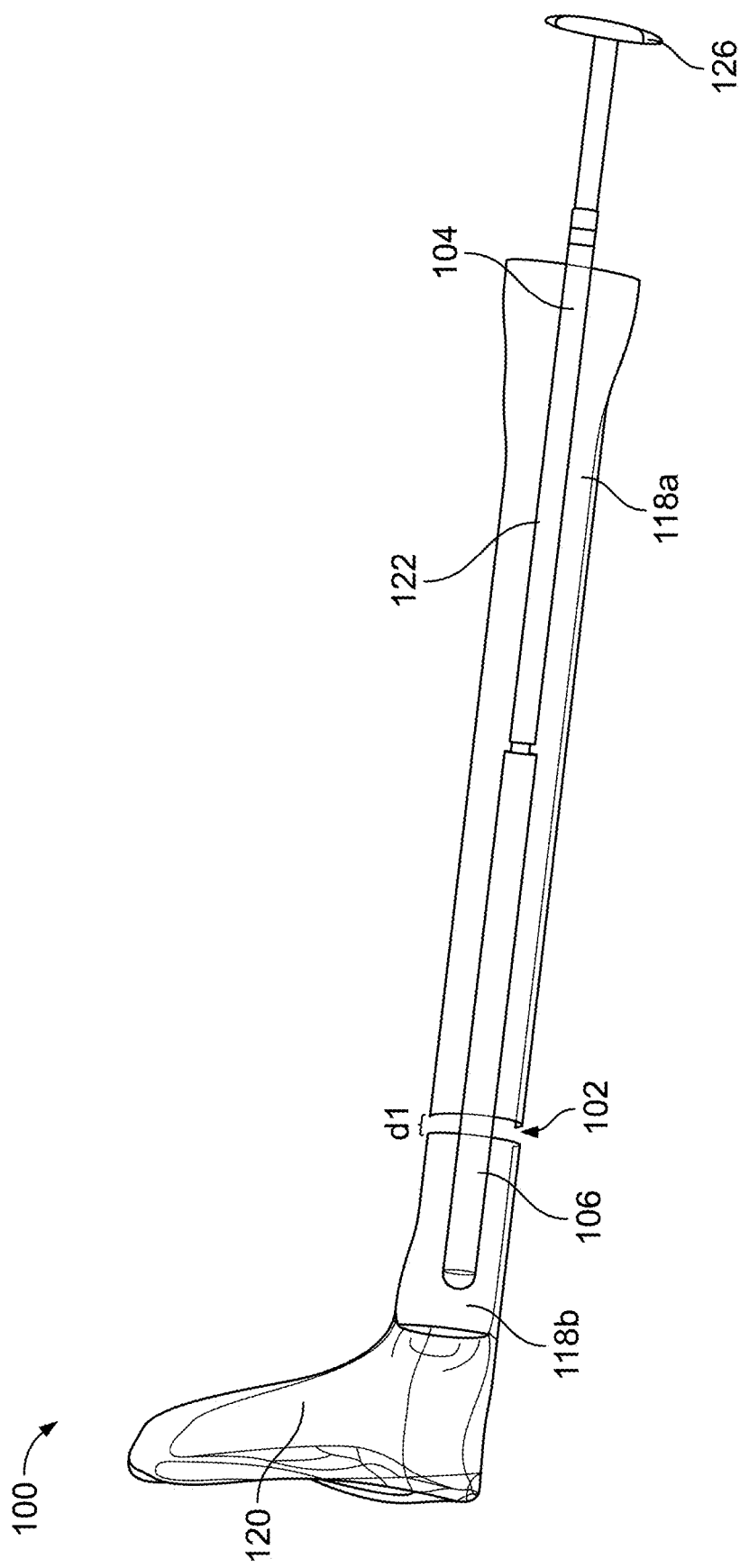
FIG. 3 is a side, partial cutaway view of an example orthopedic system including a first rotatable shaft.

Referring to FIG. 3, the first rotatable shaft 104 can be configured to push distal nail component 106 distally away from proximal nail component 122. For example, the first rotatable shaft 104 can be rotated using threading for creating a separation distance between a distal portion 118b and a proximal portion 118a of bone 114 in preparation for subsequent adjustment of the angle of the distal nail component 106 with respect to the longitudinal axis Y. FIG. 3 shows the separation distance as $d_1$. In some embodiments, separation distance $d_1$ can be an initial separation distance caused by the fracture of bone 114. The first handle 126 is coupled to the first rotatable shaft 104 and can be used by a user to rotate the first rotatable shaft 104.

Figure 4:
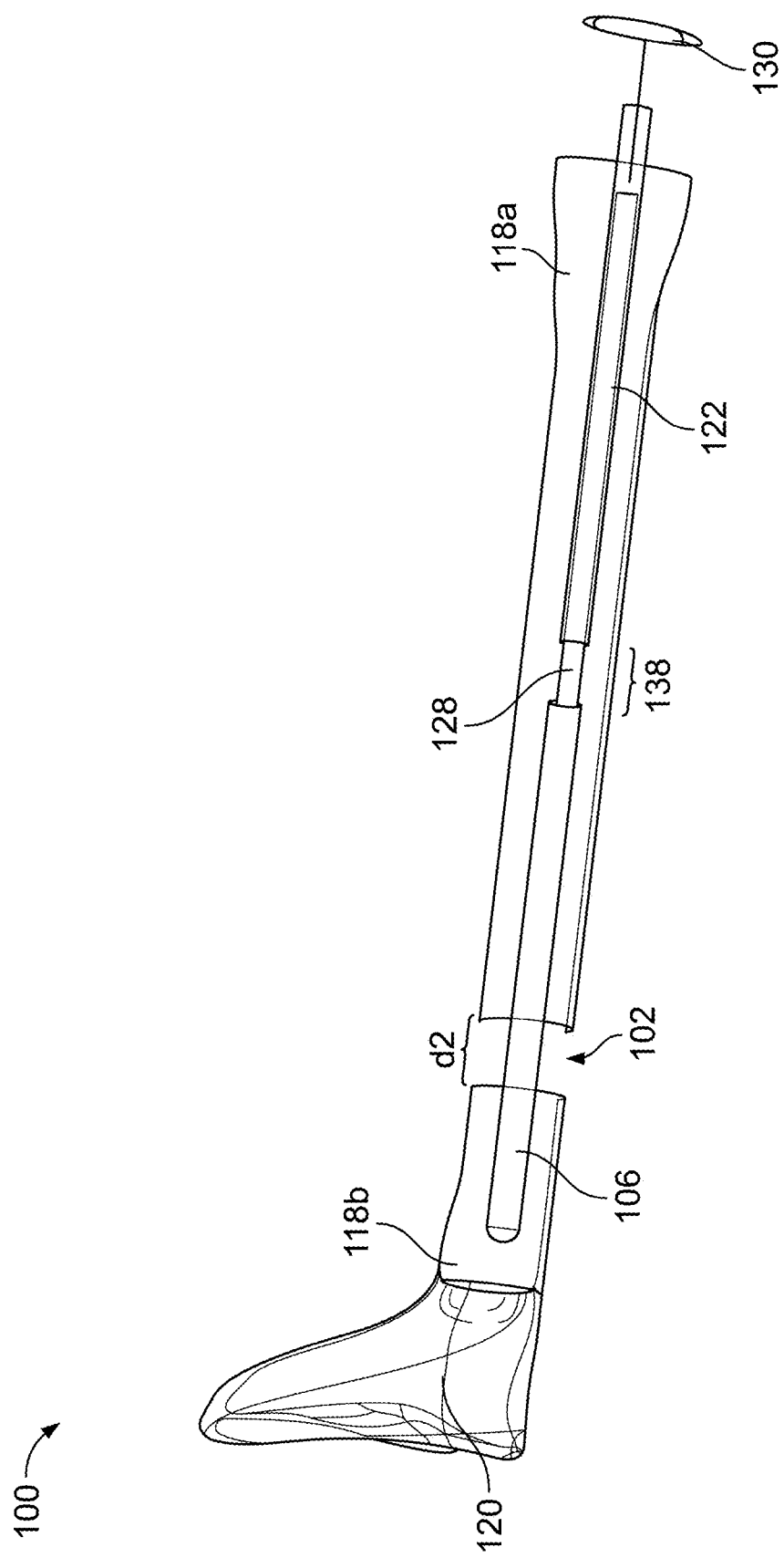
FIG. 4 is a side, partial cutaway view of an example orthopedic system including a second rotatable shaft.

FIG. 4 shows a final separation distance $d_2$ that can be created between a distal portion 118b and a proximal portion 118a of bone 114 to facilitate angle adjustment. Thus, separation distance $d_2$ can be greater than separation distance $d_1$. The second rotatable shaft 128 can be configured to adjust an angle between the distal portion 118b and the proximal portion 118a of the bone 114 to restore a natural angle of the subject. In some embodiments, the angle is about 45 degrees or less (e.g., 40 degrees or less, 35 degrees or less, 30 degrees or less, 25 degrees or less, 20 degrees or less, 15 degrees or less, 10 degrees or less, 5 degrees or less, 0 degrees or less, −5 degrees or less, −10 degrees or less, −15 degrees or less, −20 degrees or less, −25 degrees or less, −30 degrees or less, −35 degrees or less, −40 degrees or less, −45 degrees or less) with respect to the longitudinal axis Y. Distal nail component 104 can be coupled to the second rotatable shaft 128. Furthermore, the second handle 130 can be coupled to the second rotatable shaft 128 and enable a user to rotate the second rotatable shaft 128. Rotation of the second rotatable shaft 128 leads to rotation of the distal nail component 104 and thus, it leads to rotation of the distal end 118b of the bone 114.

Figure 5:
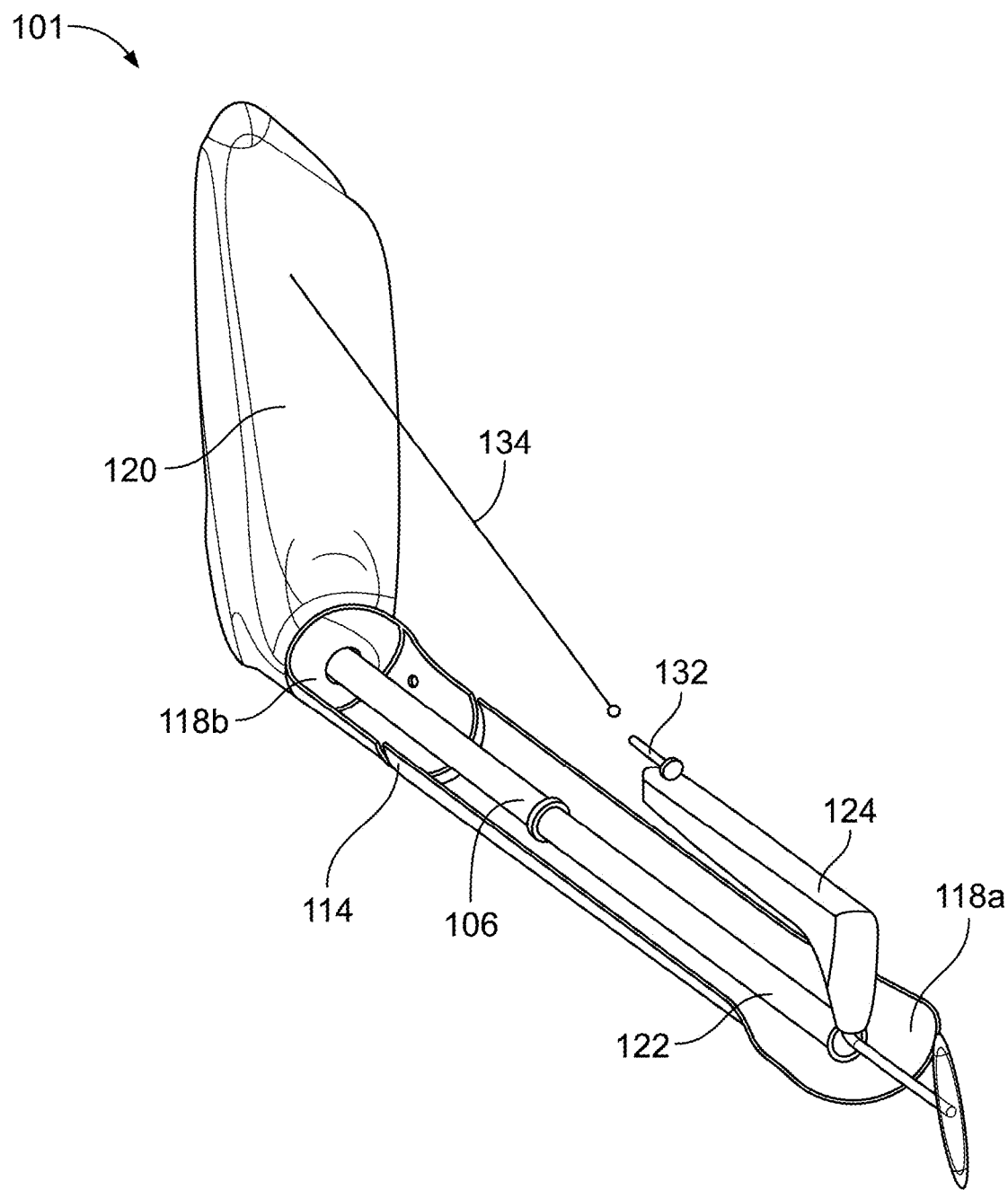
FIG. 5 is a perspective, partial cutaway view of an example orthopedic system including a laser alignment device.

Referring to FIG. 5, an example orthopedic system 101 inserted within a bone 114 having a fracture 102 is shown. The orthopedic system 101 can include an intramedullary nail 100 and a laser alignment device 132. After adjusting the angle of the proximal and distal components, the distal nail component 106 is retracted proximally to meet and interlock with the proximal nail component 122. Interlocking of the proximal and distal end components enables the intramedullary nail to maintain the desirable angle thereby, providing stabilization and weight-bearing support for the bone. The laser alignment device 132 can be mounted on the nail insertion handle 124 for guiding angle adjustment. In some embodiments, the mounting component can be retrofitted onto any of the handles. In some embodiments, the laser alignment device 132 can be reversibly mounted onto any of the handles.

Referring to FIG. 6, the disclosure provides a top and bottom two component intramedullary nail 100 (e.g., a proximal and distal nail components 122 and 106, respectively) The intramedullary nail 100 can be inserted into a fractured long bone and fixed at the distal end with screws through the bone. The intramedullary nail 100 includes a first internal rotating mechanism (e.g., the first rotatable shaft 104) that can be used to push the distal nail component 106, along with the distal portion 118b of the bone (which moves freely due to the fracture), and internally "open" the fracture site. A laser alignment device can be mounted to the nail-insertion handle and can act as a guide for positioning the foot in line with the tibia plateau, for example. The intramedullary nail 100 includes a second internal rotating mechanism (e.g., the second rotatable shaft 128) that can be used to directly fine adjust the angle of the distal limb to the normal physiological angle. The intramedullary nail 100 is designed in such way that the distal nail component 106 can move independently from the proximal nail component 122 and the angle can be adjusted with precision using a special tool inserted into the intramedullary nail 100. Once the perfect angle is determined, the angle is locked using a tapered lock 136 and the steps are done in reverse (e.g., the distal nail component 106 is retracted proximally). Thus, the intramedullary nail 100 and with it the fracture is "closed" by retracting the distal part of the nail, keeping the angle secure and locked. At this point, the outer shell 112 interlocks between the proximal and distal nail components 122 and 106, respectively, making the intramedullary nail 100 stable and allowing the fractured bone to bear weight. Finally, a cap is placed on the fully retracted nail to lock all components and avoid unintended rotation.

While a number of examples have been described for illustration purposes, the foregoing description is not intended to limit the scope of the invention, which is defined by the scope of the appended claims. There are and will be other examples and modifications within the scope of the following claims.

What is claimed is:

1. An intramedullary nail for treating a bone fracture, the intramedullary nail comprising:
    a proximal nail component defining a first longitudinal axis and a first coaxial channel;
    a distal nail component defining a second longitudinal axis that is coaxial with the first longitudinal axis;
    a rotatable shaft fixedly coupled to and extending proximally from the distal nail component, the rotatable shaft being slidably disposed within the first coaxial channel, the rotatable shaft being rotatable about the second longitudinal axis relative to the proximal nail component;
    a first handle removably coupleable at a proximal end of the proximal nail component, the first handle being rotatable about the first longitudinal axis to drive longitudinal movement of the distal nail component relative to the proximal nail component while maintaining constant rotational positions of the proximal and distal nail components relative to the first and second longitudinal axes; and
    a second handle removably coupleable at the proximal end of the proximal nail component, the second handle coupled to the rotatable shaft and being rotatable about the first longitudinal axis to drive rotation of the distal nail component about the second longitudinal axis while maintaining: (i) a constant rotational position of the proximal nail component relative to the first longitudinal axis and (ii) a constant overall longitudinal length of the intramedullary nail.

2. The intramedullary nail of claim 1, wherein the rotatable shaft is a threaded shaft.

3. The intramedullary nail of claim 2, wherein the rotatable shaft defines a channel.

4. The intramedullary nail of claim 1, wherein the intramedullary nail is extendable.

5. The intramedullary nail of claim 1, further comprising a lock for securing the rotational position of the distal nail component relative to the rotational position of the proximal nail component.

6. The intramedullary nail of claim 1, wherein the distal nail component is rotatable relative to the proximal nail component.

7. The intramedullary nail of claim 1, further comprising:
    a laser alignment device configured for guiding adjustment during the rotation of the distal nail component about the second longitudinal axis.

8. The intramedullary nail of claim 7, wherein the laser alignment device emits a laser beam.

9. The intramedullary nail of claim 8, wherein the laser beam aligns the intramedullary nail with: (i) a bone having the bone fracture, (ii) a foot of a subject having the bone fracture, (iii) an adjacent joint, or (iv) both the bone having the bone fracture and the foot of a subject having the bone fracture.

10. The intramedullary nail of claim 1, wherein the proximal nail component and the distal nail component are connected via the rotatable shaft.

11. The intramedullary nail of claim 1, further comprising a taper lock for securing the proximal nail component to the distal nail component.

12. The intramedullary nail of claim 1, wherein the distal nail component is configured to interlock with the proximal nail component.

13. A method of using an orthopedic system for treating a fractured bone of a subject, the method comprising:
    boring a bone channel in the fractured bone;
    inserting an elongate shaft of an intramedullary nail into the bone channel, wherein the elongate shaft comprises a proximal nail component defining a first longitudinal axis and a distal nail component defining a second longitudinal axis that is coaxial with the first longitudinal axis, and wherein at least a portion of the proximal nail component is inserted in the bone channel of a proximal portion of the fractured bone and at least a portion of the distal nail component is inserted in the bone channel of a distal portion of the fractured bone;
    providing a first handle that is releasably coupleable to the proximal nail component;
    rotating the first handle about the first longitudinal axis to push the distal nail component of the intramedullary nail distally relative to the proximal nail component and to increase a separation distance between the proximal and distal portions of the fractured bone;
    providing a second handle that is releasably coupleable to the proximal nail component;
    after rotating the first handle to increase the separation distance between the proximal and distal portions of the fracture bone, rotating the second handle about the first longitudinal axis to rotate the distal nail component and the distal portion of the fractured bone about the second longitudinal axis while maintaining a constant rotational position of the proximal nail component and the proximal portion of the fracture bone relative to the first longitudinal axis; and
    after rotating the second handle to rotate the distal portion of the fractured bone relative to the proximal portion of the fractured bone, rotating the first handle to retract the distal nail component and the distal portion of the fractured bone proximally towards the proximal nail component and the proximal portion of the fracture bone to decrease the separation distance and to interlock the distal nail component with the proximal nail component, wherein rotational positions of the proximal and distal portions of the fractured bone relative to the first and second longitudinal axis are held constant as the first handle is rotated to decrease the separation distance between the proximal and distal portions of the fractured bone.

14. The method of claim 13, wherein the bone is a long bone.

15. The method of claim 13, wherein the bone channel comprises a medullary canal of the fractured bone.

16. The method of claim 15, further comprising reaming the medullary canal of the fractured bone.

17. The method of claim 13, wherein the bone is a tibia, and wherein the method further comprises using a laser alignment device to act as a guide for positioning a foot in line with a tibia plateau.

18. The method of claim 13, further comprising using one or more screws to fix a distal end portion of the distal nail component to the distal portion of the fractured bone.

19. The method of claim 13, wherein an overall length of the intramedullary nail remains constant during the rotating of the second handle.

20. The method of claim 13, further comprising, after rotating the second handle to rotate the distal portion of the fractured bone relative to the proximal portion of the fractured bone, securing the rotational positions of the proximal and distal portions of the fracture bone relative to the first and second longitudinal axes.

21. The method of claim 13, further comprising, after interlocking the distal nail component with the proximal nail component, uncoupling the first handle and/or second handle from the intramedullary nail.

22. The method of claim 13, further comprising:
prior to rotating the second handle about the first longitudinal axis to rotate the distal nail component and the distal portion of the fractured bone about the second longitudinal axis, replacing the first handle with the second handle; and
prior to rotating the first handle to retract the distal nail component and the distal portion of the fractured bone proximally towards the proximal nail component and the proximal portion of the fracture bone, replacing the second handle with the first handle.

* * * * *